United States Patent [19]

Higa et al.

[11] Patent Number: 4,942,180

[45] Date of Patent: Jul. 17, 1990

[54] ANTITUMOR CHAMIGRENE DERIVATIVES AND THEIR METHODS OF USE

[75] Inventors: Tatsuo Higa, Okinawa, Japan; Kenneth M. Snader, Vero Beach, Fla.

[73] Assignee: Harbor Branch Oceanographic Institution, Inc., Ft. Pierce, Fla.

[21] Appl. No.: 772,390

[22] Filed: Sep. 4, 1985

[51] Int. Cl.$^5$ .................. A61K 31/12; C07C 49/553
[52] U.S. Cl. ................................ 514/691; 568/367
[58] Field of Search ....................... 514/691; 568/367

[56] References Cited

U.S. PATENT DOCUMENTS 4,162,308  7/1979  Calvin et al. .................. 424/195.1
4,162,309  7/1979  Calvin et al. .................. 424/195.1

OTHER PUBLICATIONS

*Bull. Chem. Soc. Jpn.*, 56 (No. 12), pp. 3824–3826 (1983), M. Suzuki et al.
*Tetrahedron Letters*, No. 26, 1973, Pergamon Press (GB), A. G. Gonzalez et al., pp. 2381–2384.
*Tetrahedron Letters*, No. 23, 1974, Pergamon Press (GB), J. A. McMillam et al., pp. 2039–2042.
*Tetrahydron Letters*, No. 4, 1975, Pergamon Press (GB), S. M. Waraskiewicz et al., pp. 281–284.
*Tetrahydron Letters*, No. 35, 1976, Pergamon Press (GB), A. G. Gonzaleaz et al., pp. 3051–3054.
*Tetrahedron*, vol. 35 (1979), Hollenbeak et al., pp. 541–545.
*Planta Medica*, vol. 44 (1982), Gonzaleaz et al., pp. 44≠46.
Suzuki et al., Bull. Chem. Soc. Jpn, 56(WO. 12), pp. 3824–3826 (1983) (a copy is needed).

*Primary Examiner*—Jerome D. Goldberg
*Attorney, Agent, or Firm*—Carroll F. Palmer

[57] ABSTRACT

This invention relates to antitumor compositions, and a method for inhibiting, remitting or controlling the growth of tumors or tumor cells utilizing antitumor compositions. More particularly, the antitumor compositions comprise, as active ingredient, an antitumor effective amount of halogenated chamigrenes extracted and derived from red alga and sea hares which diet upon red alga.

6 Claims, No Drawings

ANTITUMOR CHAMIGRENE DERIVATIVES AND THEIR METHODS OF USE

FIELD OF THE INVENTION

This invention relates to compositions comprising, as active ingredients chamigrene derivatives, which have newly discovered and useful biological activity. More particularly, this invention relates to pharmaceutical compositions comprising, as active ingredients, chamigrene derivatives which are derived from marine organisms, e.g., red alga and sea hares which diet upon red alga.

BACKGROUND OF THE INVENTION

The term tumor refers to abnormal masses of new tissue growth which is discordant with the economy of the tissue of origin or the host's body as a whole. Tumors are common in a variety of mammals and the prevention, control of the growth and regression of tumors in mammals is important to man.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

U.S. Pat. Nos. 4,162,308 and 4,162,309 to Calvin and Ellis describe that water soluble extract from marine red alga have been found to be effective to inhibit the growth of certain herpes viruses.

U.S. Pat. No. 4,162,308 describes water soluble extracts from marine red alga selected from a group consisting of *Turnella mertensiana, Schizymenia epiphytica, Turnerella pennyi* algae and mixtures thereof as effective to inhibit the growth of herpes simplex virus, type 1 and type 2, and herpes zoster, and to relieve the pain caused by infection attributable to such viruses.

U.S. Pat. No. 4,162,309 describes the use of water soluble extracts from marine red alga selected from a group consisting of *Neodilsea americana* and *Neodilsea integra* algae and mixtures thereof to inhibit the growth of herpes simplex virus, type 1 and type 2, herpes zoster, and to relieve the pain caused by infection attributable to such viruses In addition to the water soluble red alga extracts described in the above noted U.S. patent applications to Calvin and Ellis other compounds have been isolated from red alga and marine organisms known as sea hares which are mollusks which diet on red algae. These compounds include halogenated chamigrenes and have been described in various literature references including P. J. Scheuer, Ed. *Marine Natural Products* Volume 1 (Martin), 1978 and Volume 5 (Erickson), 1983 Academic Press, the entire disclosure of this reference is hereby incorporated herein by reference.

Co-pending applications of the present inventors relate to red alga and sea hare extracts and derivatives thereof comprising certain chamigrenes which show antiviral activity and certain cyclohexadienones which show antiviral and antitumor activity i.e., U S. patent applicant Ser. Nos. 682,896; 682,278, now abandoned, and 744,620, respectively. The entire disclosures of these three patent applications are hereby incorporated herein by reference.

In an article entitled "Structures of Halogenated Chamigrene Derivatives, Minor Constituents From the Red Alga Laurencia nipponica Yamada" appearing at *Bull Chem Soc Jpn.*, 56 (no. 12) at Pp 3824–3826, (1983); the authors, Minoru Suzuki, Makoto Segawa, Teruaki Suzuki, and Etsuro Kurosawa of the Department of Chemistry, Faculty of Science, Hokkaido University, Sapporo 060, Japan, disclose various compounds derived from red alga Laurencia nipponica. These compounds include halogenated chamigrenes and methods of their isolation and preparation. No disclosure has been made by Suzuki et al. of the bioacctivity of these compounds. The entire disclosure of the Suzuki et al article is incorporated herein by reference.

One of the compounds prepared by Suzuki et al and disclosed in the above-mentioned article having the structure:

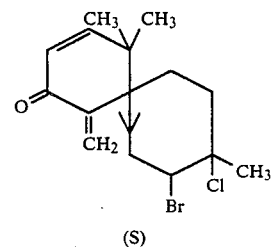

(S)

was supplied by Suzuki et al and examined by the present inventors, along with other halogenated chamigrene compounds, for biological activity.

It has now been found that certain chamigrene extracts from marine organisms such as red alga and sea hares which diet upon red alga, possess useful biological activity.

SUMMARY OF THE INVENTION

Objects and advantages of the invention will be set forth, in part, in the description which follows and in part will be obvious from this description, or may be learned by the practice of the invention. The objects and advantages of the invention are realized and attained by means of the compositions, processes, methods, and the combinations particularly pointed out in the appended claims.

To achieve the objects in accordance with the purposes of the invention, as embodied and fully described herein, the invention comprises an composition comprising a non-toxic pharmaceutically acceptable carrier or diluent and, as active ingredients, an effective amount of one or more compositions of the general formula (I–V):

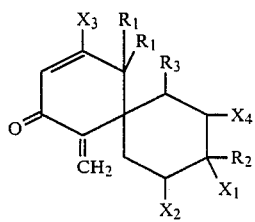

I

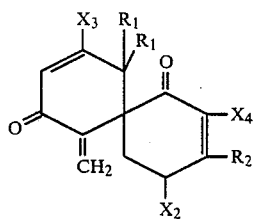

II

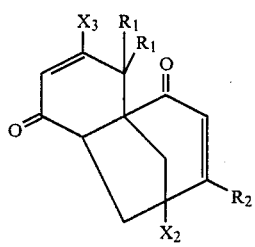

III

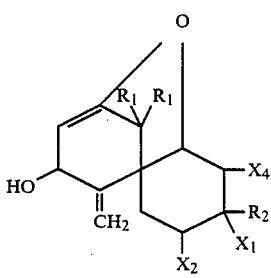

IV

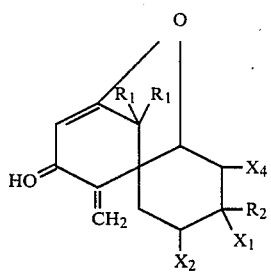

V wherein both $R_1$ are the same and are hydrogen or a lower alkyl group; $R_2$ is a lower alkyl group; $R_3$ is hydrogen, a halogen, $SR_4$, $NR_4$, hydroxy or acetoxy group, wherein, $R_4$ is H or a lower alkyl group; and $X_1$, $X_2$, $X_3$, and $X_4$ are the same or different and are a hydrogen, hydroxy, fluoro, chloro, bromo, iodo or lower alkoxy group with the proviso that for formula I when $X_1$ is chloro, $X_2$ is bromo, $X_4$ is hydrogen, $R_1$ is methyl, and $R_3$ is hydrogen: $X_3$ is not a hydrogen or bromo group.

In preferred embodiments of the invention, subject to the above proviso, the lower alkyl and acyl groups have from 1 to 5 carbon atoms and $X_1$, $X_2$, $X_3$ and $X_4$ are the same or different and are a hydrogen, chloro or bromo group.

In a more preferred embodiment of the invention, the active ingredient of the composition comprises one or more compositions of the formula:

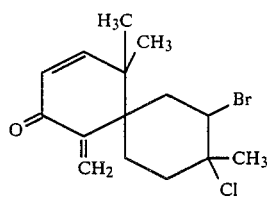

VI

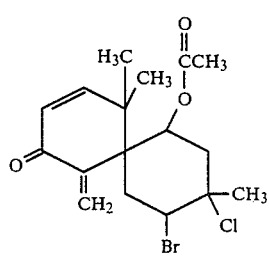

VII

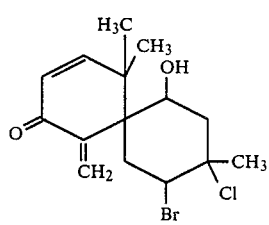

VIII

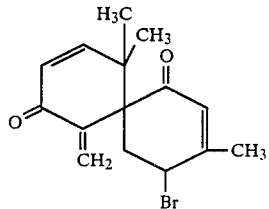

IX

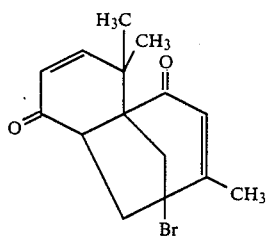

X

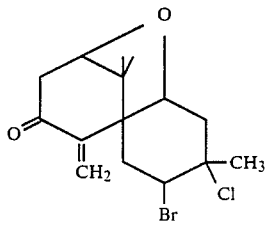

XI

-continued

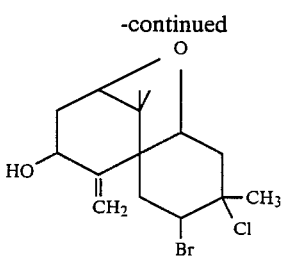
XII

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention an antitumor composition is provided comprising a non-toxic pharmaceutically acceptable carrier or diluent and, as active ingredients, an effective amount of one or more of the compositions of the formula (I–V):

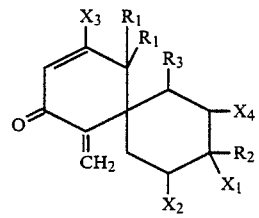
I

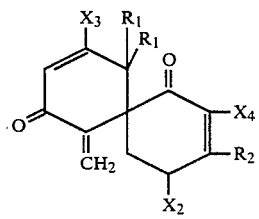
II

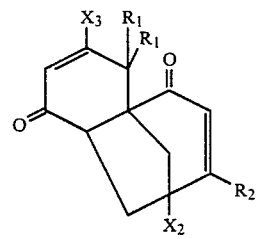
III

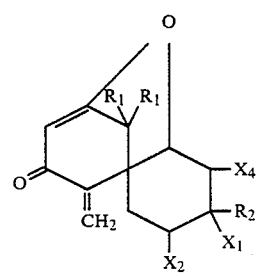
IV

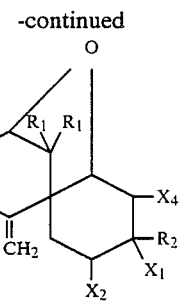
V wherein both $R_1$ are the same and are hydrogen or a lower alkyl group; $R_2$ is methyl; $R_3$ is a halogen, $SR_4$, $NR_4$, hydroxy or acetoxy group wherein, $R_4$ is H or a lower alkyl group; and $X_1$, $X_2$, $X_3$, and $X_4$ are the same or different and are a hydrogen, hydroxy, fluoro, chloro, bromo, iodo or lower alkoxy group with the proviso that for formula I when $X_1$ is chloro, $X_2$ is bromo, $X_4$ is hydrogen, $R_1$ is methyl and $R_3$ is hydrogen: $X_3$ is not a hydrogen or a bromo group.

In preferred embodiments of the invention, the lower alkyl and acyl groups have from 1 to 5 carbon atoms and $X_1$, $X_2$, $X_3$, and $X_4$ are the same or different and are a hydrogen, chloro or bromo groups.

Particularly preferred embodiments of the invention include the following:

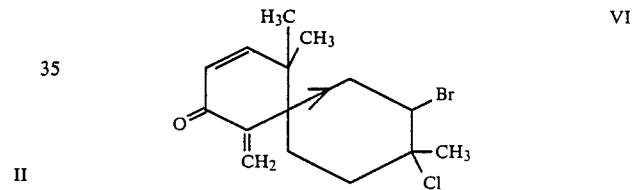
VI

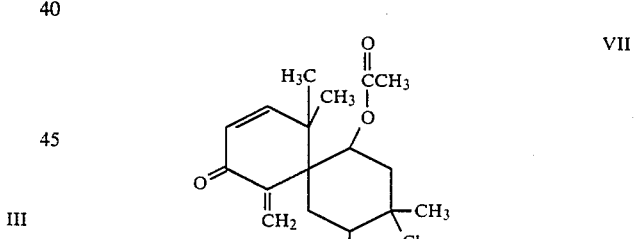
VII

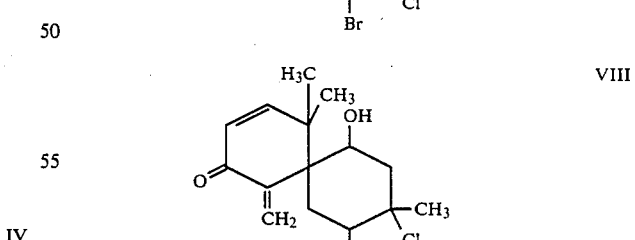
VIII

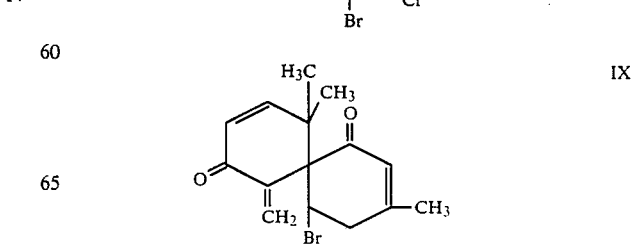
IX

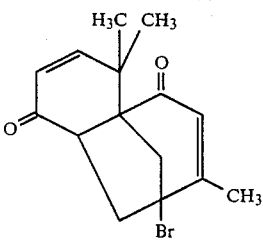

X

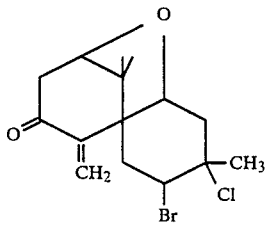

XI

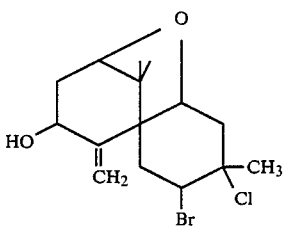

XII

Useful examples of non-toxic pharmaceutically acceptable carrier or diluents include, but are not limited to, the following: ethanol; dimethyl sulfoxide; and glycerol.

A source for and process to produce compounds of the invention as defined most broadly by Formula I is described for particular compounds in the example section which follows and other general methods are described in the Suzuki et al article, and the co-pending applications of Higa and Snader identified and incorporated herein, supra. Sources of useful pharmaceutically acceptable carriers or diluents would be known to those skilled in the pharmaceutical art.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention. The starting materials and reagents in the examples whose method of preparation are not indicated, are commercially available from sources known to the art such as chemical supply houses.

EXAMPLE 1

Preparation of compound (1):

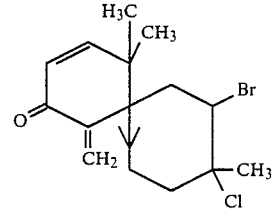

6 individual sea hares (a mollusk *Aplysia doctylomela*) (approximately 360 grams each) were collected at Hisamatsu, Miyako Island, Okinawa where they were observed to be dieting upon red algae genus Laurencia. The digestive gland of the sea hares were removed and collected (about 115 gms total). The glands were placed in a suitable vessel and 300 ml. of acetone was added to the vessel and the mixture was homogenized to produce a slurry.

The slurry was filtered to provide an acetone extract and this was extracted twice more with 500 ml. of acetone. The acetone extract was concentrated under vacuum at room temperature. The concentrated acetone extract yielded an aqueous suspension which was admixed with 300 ml. of hexane in a separatory funnel. The hexane fraction was extracted for a total of three times with 300 ml. fractions of hexane and the hexane removed to yield 3.8 gms of crude product oil.

The hexane soluble extract was fractionated on a silica gel column, with a 3:1 hexane/chloroform eluent, into five fractions (A-E).

Fraction C was separated on a TLC-grade silica gel column (1:3 hexane-chloroform) into five fractions (C-1 to C-5). Fraction C-1 was again passed through the same column (10:1 hexane-ethyl acetate), and fractions giving a UV-active spot on TLC were collected and purified by running on a Lobar Si-60 column (5:1 hexane-ethyl acetate) to give 38 mg of compound (1) as light yellow glass. Crystallization of this material from hexane-carbon tetrachloride gave colorless crystals, mp 98°-100° C.; IR (Film) 2970, 1675, 1620, 1380, 1260, 1095, 845, and 755 cm$^{-1}$.

EXAMPLE 2

Preparation of Compound (2):

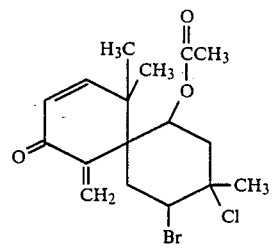

Fraction C-4 from Example 1 was passed on a polystyrene column (methanol) to remove greenish pigment. The resulting methanol eluate (yellow oil) was chromatographed on a silica gel column (7:3 hexane-ethyl acetate) into 17 fractions. Fractions containing a UV-active spot were combined and again run on the same column with the same solvent to yield crystalline material. Recrystallization of the material from hexane-chloroform gave 204 mg of compound (2) as colorless crystals, mp 105°-106° C.; IR(KBr) 2970, 1735, 1678, 1610, 1370, 1235, 1040, 1020, 940, and 842 cm$^{-1}$.

Alternatively, compound 2 may be isolated from Red alga, Laurencia by the following method. Red alga Laurencia SP. (9.5 kg), collected at Hisamatsu, Miyako Island, Okinawa, was freeze-dried and extracted with acetone (6×5L). The extract was concentrated, and the residue was partitioned between ethyl acetate and water to give 19.9 g of ethyl acetate soluble oil.

A part (2.46 g) of this oil was chromatographed on silica gel column by eluting with chloroform the middle part of the fractions was further separated on a polystyrene gel column (MeoH-H$_2$O 20:1) to give 360 mg of light yellow oil. Repeated chromatography over silica gel column (CHCl$_3$) gave 85 mg of Compound 2 as colorless crystals.

EXAMPLES 3 and 4

Preparation of compound (3) and (4) by saponification of compound (2)

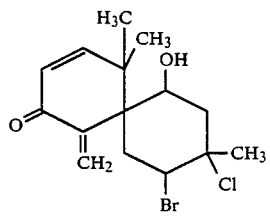
(3)

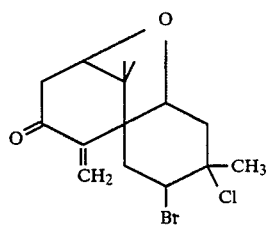
(4)

A solution of compound (2) from Example 2 (81.0 mg) in 2 ml of 1% KOH in 95% ethanol was allowed to stand at room temperature for 30 min. The solution was acidified with ethanolic hydrochloric acid to pH 4, concentrated, and separated on a small silica gel column (CHCl$_3$) to give 21.8 mg (31.7%) of alcohol (3) and 47.3 mg (65.8%) of ether (4).

Alcohol (3) was recrystallized from hexanne-chloroform to give colorless needles, mp 174°–176° C.; IR(KB) 3300(br), 2920, 1660, 1605, 1450, 1400, 1375, 1310, 1270, 1100, 1040, 1010, 975, 950, and 835 cm$^{-1}$.

Ether (4) was recrystallized from hexanne-chloroform to give colorless prisms, mp 144°–145° C.; IR(KBr) 2910, 1690, 1600, 1390, 1205, 1140, 1120, 1095, 1040, 1000, 960, 865, 805, and 790 cm$^{-1}$.

Alternate Preparation of compound (4) by acid treatment of alcohol (3)

A solution of compound 3 from Example 3 (24.4 mg) and 2.1 mg of p-toluenesulfonic acid in benzene (2 ml) was heated at reflux for 3 hr. The mixture was poured onto a small silica gel column and eluted with chloroform to yield 21.6 mg (88.5%) of ether (4) mp 144°–145° C.

EXAMPLE 5

Preparation of compound (5)

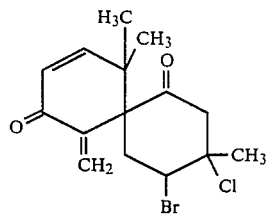
(5)

To a solution of alcohol (3) from Example 3 (22.9 mg) in acetone (2 ml) was added a few drops of Jones reagent, and the mixture was stirred at room temperature for 10 min and directly poured onto a small silica gel column to give 15.7 mg (68.2%) of diketone. Recrystallization from hexane-chloroform gave a ketone of Formula Y as colorless, fine needles, mp 122°–129° C.

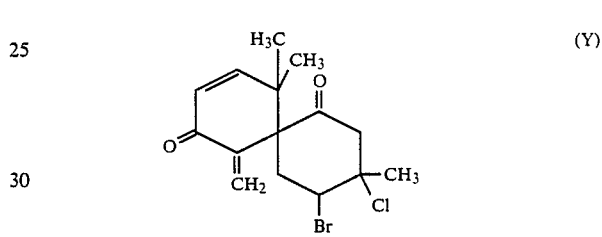
(Y)

A solution of ketone Y (37.3 mg) in 2 ml of 0.1% KOH in 95% ethanol was allowed to stand at room temperature for 1 hr. The solution was acidified with ethanolic hydrochloric acid to pH 4, concentrated, and separated on a Lobar Si-60 column (CHCl$_3$) to give 24.3 mg (72.8%) of (5) as colorless crystals, after recrystallization from hexane-chloroform, mp 119°–120° C.; IR(KBr) 2950, 1660, 1615, 1400, 1375, 1305, 1285, 1250, 1210, 1160, 1120, 850, and 775 cm$^{-1}$.

EXAMPLE 6

Preparation of compound (6)

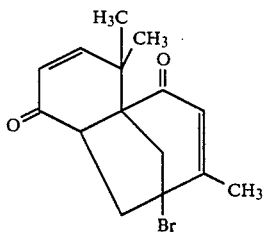
(6)

A solution of ketone Y from Example 5 (16.3 mg) in 2 ml of 0.5% KOH in 95% ethanol was allowed to stand at room temperature for 12 min. The mixture was acidified with ethanolic hydrochloric acid to pH 4, concentrated, and separated by TLC (silica gel, hexane-CHCl$_3$ 1:2) to furnish 7.5 mg (51.7%) of (7) as colorless needles, after recrystallization from hexane-chloroform, mp 124.5°–127° C.; IR(KBr) 2930, 1660, 1620, 1460, 1370, 1270, 1215, 1120, 1075, 940, 870, and 805 cm$^{-1}$.

EXAMPLE 7

Preparation of compound (7)

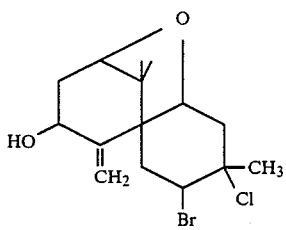

(7)

To a stirred mixture of 47.7 mg of compound (4) from example 4 in methanol (1 ml) and 0.4 M $CeCl_3$ in methanol (1 ml) was slowly added $NaBH_4$ (20 mg) in methanol (1 ml) at 0°. Stirring was continued for an additional 8 min. The reaction mixture was quenched with 0.3 ml of acetone and the residual inorganic material was removed by passing through a short column of silica gel (ca 1 g) with chloroform EtOAc to give 43.5 mg (92%) of alcohol (7) as colorless prisms from hexane chloroform mp 158°-160°; IR(KBr) 3440, 2925, 1460, 1385, 1035, 915 $cm^{-1}$.

EXAMPLE 8

Compound (S) was obtained from the authors of the Suzuki et al article which was prepared in the general manner described in the Suzuki et al publication experimental section which has been incorporated by reference herein (supra).

Antitumor Activity of the Compounds of the Invention

The following assay method was utilized to illustrate the antitumor effectiveness of compounds of formulae I-XII:

L1210 AND P388 MURINE LEUKEMIA CELL
AND MCF-7 HUMAN MAMMARY
CARCINOMA CYTOXICITY ASSAY
24-WELL PLATE SCREENING ASSAY AND
TUBE ASSAY PROTOCOL

MATERIALS UTILIZED

Media - Dulbeccos with glucose and pyruvate (Biologos, Inc) with 10% horse serum, (Biologos, Inc) and 1.0 µg/ml gentamicin (Gibco)

Cells - L1210 and P-388 mouse leukemia cells (American Type Culture Collection) in media at a concentration of $5 \times 10^4$ cells/ml. Sterile 24-well culture plates (nunc) for screening or $12 \times 75$ mm glass culture tubes (Becton-Dickinson) for tube assay. Microdispenser with 1 to 5 µl increments (Drummond Scientific Co. Broomall Pa.). Finnpipette with 5 to 50 µl increments and Finnpipette with 50 to 200 µl increments.

PROCEDURE

1. A sample of the composition to be assayed is added to each well or tube in an amount of from 200 µg/ml and 100 µg/ml for screening. For DDC of known active compounds use log concentrations from 100 µg/ml to 0.01 µg/ml for range-finding assay; when range has been determined, use five concentrations between highest and lowest active concentrations.

2. Add 2.0 ml of $5 \times 10^4$ cell suspension in media to each well or tube. Tubes are loosely covered with parafilm.

3. Incubate in 5% $CO_2$ incubator 48 hours.

4. Visually read plates with inverted microscope, comparing with solvent control. Assign activity as follows:
   0 = 90−100% of control growth
   1+ = 75−89% of control growth
   2+ = 50−74% of control growth
   3+ = 25−49% of control growth
   4+ = 25% of control growth Repeat all positive samples using tube assay.

5. For Tube assays - Mix tube well on vortex and remove 0.5 ml aliquot and add to 9.5 ml nf diluent fluid (Isoton-Couter) in Accuvette (Coulter) and mix well by inversion immediately before counting, taking care not to produce excessive bubbles. Count on Coulter Counter (Counter is set to count 0.5 ml of the solution; therefore counts may be converted to cell/ml in original assay tube by multiplying count by 40. Positive control - Vinblastine or Vincristine in aqueous solution. Final Conc. of Vinblastine or Vincristine control (use 2 µl/assay)

| Solution Conc. | Amt added | Final Conc. in tets |
|---|---|---|
| 100 mg/ml | 2 ul | 100 ug/ml |
| 10 mg/ml | 2 ul | 10 ug/ml |
| 1 mg/ml | 2 ul | 1 ug/ml |

Notes:
For solvents other than water, allow solvent to evaporate from tube or well in hood.

Chloroform and butanol cannot be used in the plastic 24-well plates—use glass tubes. Always run a solvent control in duplicate in the last two wells of each plate or four tubes for each rack of 72 or less tubes. Also run four wells or tube with media and cells only per run of plates or tubes. When using volumes of aqueous solutions greater than 200 µl, dry sample and bring up to desired concentration in media.

The results of the above assay show compounds of formulae II, III, and IV are cytotoxic in vitro against L-1210, P-388 murine leukemia cells and MCF-7 Human Mammary Carcinoma Cells. The following table summarizes the results of the above assay for compounds of formula II, III and IV.

| Composition of Formula | Concentration | P388 | MCH-7 | A549* | MCH-8* |
|---|---|---|---|---|---|
| (S) | 100 | 4+ | NT | NT | NT |
|  | 10 | 2+ | 4+ | NT | NT |
|  | 1 | ND | 2+ | NT | NT |
| 1 | 100 ug/ml | 4+ | NT | 4+ | 4+ |
|  | 10 | 1+ | 4+ | 1+ | 1+ |
|  | 1 | ND | 1+ | ND | ND |
| 2 | 100 ug/ml | 4+ |  | 2+ | 3+ |
|  | 10 | ND |  | ND | ND |
|  | 1 | ND |  | ND | ND |
| 3 | 100 ug/ml | 3+ |  | 1+ | 2+ |
|  | 10 | ND |  | ND | ND |
|  | 1 | ND |  | ND | ND |
| 4 | 100 ug/ml | NT |  | 4+ | 3+ |
|  | 10 | ND |  | ND | ND |
|  | 1 | ND |  | ND | ND |
| 5 | 100 ug/ml | 4+ |  | 4+ | 4+ |
|  | 10 | 4+ |  | 4+ | 4+ |
|  | 1 | 4+ |  | 1+ | 4+ |
| 6 | 100 ug/ml | 4+ |  | 4+ | 4+ |
|  | 10 | 2+ |  | 3+ | 1+ |
|  | 1 | ND |  | 1+ | ND |
| 7 | 100 ug/ml | 1+ |  | ND | ND |
|  | 10 | ± |  | ND | ND |

-continued

Table of Antitumor Activity Against Specific Tumor Cells

| Composition of Formula | Concentration | P388 | MCH-7 | A549* | MCH-8* |
|---|---|---|---|---|---|
| | 1 | ND | | ND | ND |

*A549 and MCH-8 Activity was tested at a concentration of 50 ug/ml in lieu of 100 ug/ml.
N.D. is Not Detectable.
N.T. is Not Tested.

The scope of the present invention is not limited by the description, examples, and suggested uses herein and modifications can be made without departing from the spirit of the invention. Thus, it is intended that the present invention cover the modifications and variations of this invention provided that they come within the scope of the appended claims and their equivalents.

What is claimed is:

1. A composition of the formula I or II:

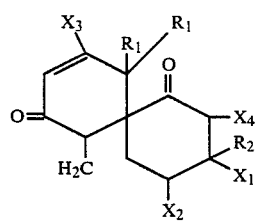
I

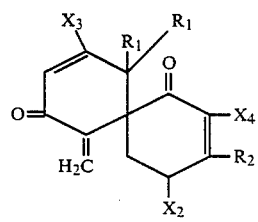
II wherein both $R_1$ groups are the same and are —H or —A,

A is lower alkyl, $R_2$ is —H or —A, $X_1$, $X_2$, $X_3$ and $X_4$ are the same or different and are —H, —OH, —F, —Cl, —Br, —I or —OA.

2. The compound of the formula:

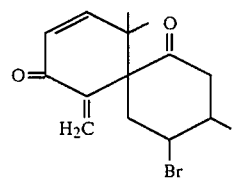

3. The compound of the formula:

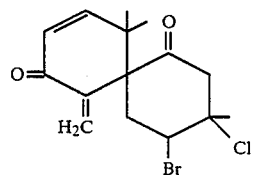

4. A pharmaceutical composition comprising as an active ingredient a pharmaceutically effective amount of at least one compound of the formula I or II:

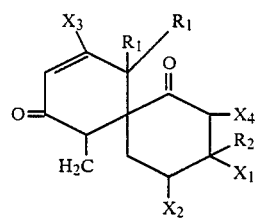
I

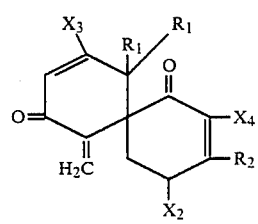
II wherein both $R_1$ groups are the same and are —H or —A,

A is lower alkyl, $R_2$ is —H or —A, $X_1$, $X_2$, $X_3$ and $X_4$ are the same or different and are —H, —OH, —F, —Cl, —Br, —I or —OA and a non-toxic pharmaceutically acceptable carrier or diluent.

5. An pharmaceutical composition comprising as an active ingredient a pharmaceutically effective amount of the compound of claim 2 and a non-toxic pharmaceutically acceptable carrier or diluent.

6. An pharmaceutical composition comprising as an active ingredient a pharmaceutically effective amount of the compound of claim 3 and a non-toxic pharmaceutically acceptable carrier or diluent.

* * * * *

UNITED STATES PATENT AND TRADEMARK OFFICE
CERTIFICATE OF CORRECTION

PATENT NO. : 4,942,180

DATED : July 17, 1990

INVENTOR(S) : Tatsuo Higa, Kenneth M. Snader

It is certified that error appears in the above-identified patent and that said Letters Patent is hereby corrected as shown below:

Column 3:

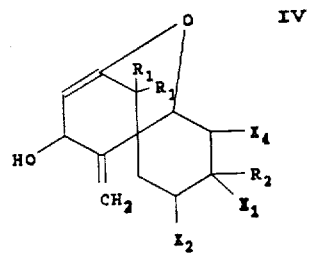 should read 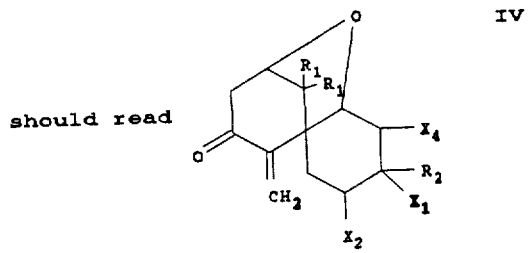

Column 3:

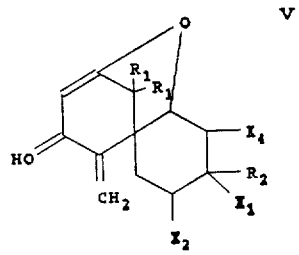 should read 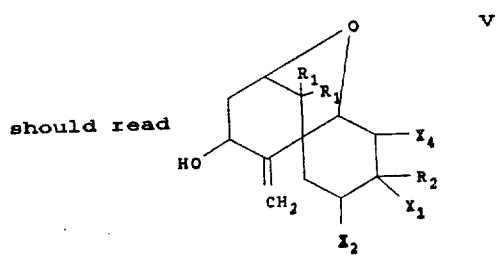

UNITED STATES PATENT AND TRADEMARK OFFICE
CERTIFICATE OF CORRECTION

PATENT NO. : 4,942,180

DATED : July 17, 1990

INVENTOR(S) : Tatsuo Higa, Kenneth M. Snader

It is certified that error appears in the above-identified patent and that said Letters Patent is hereby corrected as shown below:

Column 5: 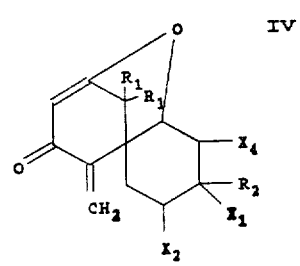   should read   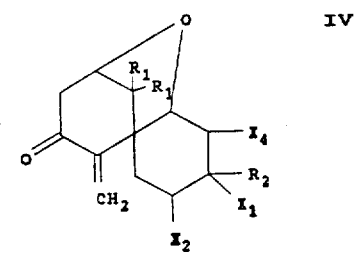

Column 6: 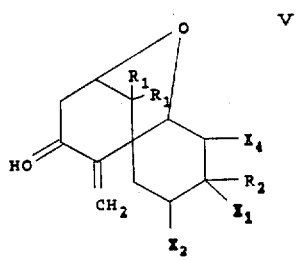   should read   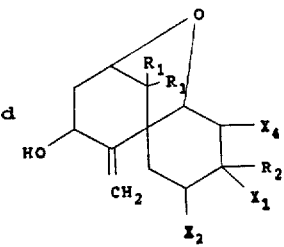

UNITED STATES PATENT AND TRADEMARK OFFICE
CERTIFICATE OF CORRECTION

PATENT NO.    :   4,942,180

DATED         :   July 17, 1990

INVENTOR(S)   :   Tatsuo Higa, Kenneth M. Snader

It is certified that error appears in the above-identified patent and that said Letters Patent is hereby corrected as shown below:

Column 10:

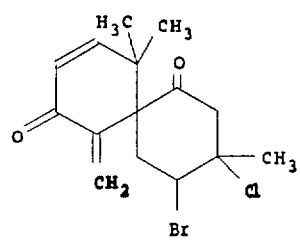 should read 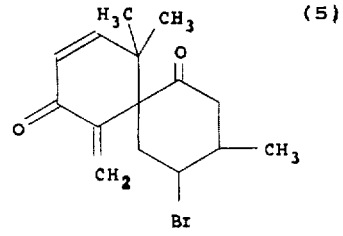

Signed and Sealed this

Second Day of July, 1991

Attest:

HARRY F. MANBECK, JR.

*Attesting Officer*   *Commissioner of Patents and Trademarks*